US012746097B2

(12) United States Patent
Hellstern et al.

(10) Patent No.: US 12,746,097 B2
(45) Date of Patent: Sep. 29, 2026

(54) SYSTEM FOR SUPPORTING A SURGEON

(71) Applicant: HELLSTERN MEDICAL GMBH, Wannweil (DE)

(72) Inventors: Sabrina Hellstern, Wannweil (DE); Claudia Sodha, Gechingen (DE); Alexander Strobel, Haigerloch-Stetten (DE); Harald Rager, Bisingen-Wessingen (DE)

(73) Assignee: HELLSTERN MEDICAL GMBH, Wannweil (DE)

( * ) Notice: Subject to any disclaimer, the term of this patent is extended or adjusted under 35 U.S.C. 154(b) by 155 days.

(21) Appl. No.: 18/696,854

(22) PCT Filed: Sep. 21, 2022

(86) PCT No.: PCT/EP2022/076253
§ 371 (c)(1),
(2) Date: Mar. 28, 2024

(87) PCT Pub. No.: WO2023/052221
PCT Pub. Date: Apr. 6, 2023

(65) Prior Publication Data

US 2024/0398503 A1 Dec. 5, 2024

(30) Foreign Application Priority Data

Sep. 30, 2021 (DE) ..................... 10 2021 125 480.9

(51) Int. Cl.
*A61B 90/60* (2016.01)
*A47C 7/58* (2006.01)
*A47C 9/00* (2006.01)

(52) U.S. Cl.
CPC ................ *A61B 90/60* (2016.02); *A47C 7/58* (2013.01); *A47C 9/005* (2013.01)

(58) Field of Classification Search
CPC ............ A61B 90/60; A47C 7/58; A47C 9/005
(Continued)

(56) References Cited

U.S. PATENT DOCUMENTS 2,570,631 A * 10/1951 Arrasmith ............ A47D 15/006 297/484
3,321,247 A * 5/1967 Dillender ............. A47D 15/006 297/484
(Continued)

FOREIGN PATENT DOCUMENTS

CN 205386189 U 7/2016
CN 205988336 U 3/2017
(Continued)

OTHER PUBLICATIONS

German Decision to Grant for corresponding DE Application No. 10 2021 125 480.9; Mailing Date, Oct. 9, 2023.
(Continued)

*Primary Examiner* — Jose V Chen
(74) *Attorney, Agent, or Firm* — CANTOR COLBURN LLP

(57) ABSTRACT

The system according to the present disclosure is used to support a surgeon. It includes an operating chair and a restraining device for the surgeon. The restraining device has a harness system which comprises at least a first and a second restraining belt which are connected to at least a first and a second spaced-apart suspension point of a traction device, the traction device being configured to establish the distance between the suspension points. The system according to the present disclosure improves the wearing comfort of the restraining device for the surgeon, since it prevents the restraining harnesses of the harness system from constricting
(Continued)

under tensile load, which can lead to unpleasant and undesirable pressure sensations in the upper body area of the surgeon.

17 Claims, 7 Drawing Sheets

(58) Field of Classification Search
USPC ....... 297/314, 464, 468, 474, 479, 483, 484, 297/486
See application file for complete search history.

(56) References Cited

U.S. PATENT DOCUMENTS

| | | | | | |
|---|---|---|---|---|---|
| 3,385,633 | A * | 5/1968 | Aizley | B60R 22/26 | 297/484 |
| 3,428,029 | A * | 2/1969 | Klickstein | B60R 22/105 | 297/484 |
| 3,754,787 | A | 8/1973 | Garber | | |
| 4,226,474 | A * | 10/1980 | Rupert | B60R 22/105 | 297/484 |
| 4,981,306 | A * | 1/1991 | Young | B62J 1/28 | 297/484 |
| 5,649,744 | A * | 7/1997 | Apodaca | B60R 22/02 | 297/484 |
| 5,660,445 | A * | 8/1997 | Murray | A61F 5/3776 | 297/484 |
| 6,095,613 | A * | 8/2000 | Ostrander | A47D 13/105 | 297/484 |
| 6,109,698 | A * | 8/2000 | Perez | B60N 2/2812 | 297/484 |
| 6,224,154 | B1 | 5/2001 | Stoki | | |
| 6,893,098 | B2 | 5/2005 | Kohani | | |
| 7,144,085 | B2 * | 12/2006 | Vits | B60N 2/265 | 297/483 |
| 8,011,730 | B2 * | 9/2011 | Greenwood | B60N 2/42709 | 297/468 |
| 8,911,013 | B2 * | 12/2014 | Reinck | B60N 2/24 | 297/484 |
| 8,973,945 | B2 * | 3/2015 | Seidenberger | B60R 22/18 | 280/808 |
| 2004/0169411 | A1 * | 9/2004 | Murray | B60R 22/105 | 280/801.1 |
| 2005/0073186 | A1 * | 4/2005 | Kohani | A47C 7/425 | 297/464 |
| 2005/0194830 | A1 | 9/2005 | Kohani | | |
| 2009/0066146 | A1 * | 3/2009 | Singh | B60R 22/10 | 297/468 |
| 2010/0078908 | A1 * | 4/2010 | Pos | B62B 9/24 | 280/47.38 |
| 2013/0307313 | A1 * | 11/2013 | Greenwood | B60R 22/322 | 297/468 |
| 2014/0125110 | A1 * | 5/2014 | Kennedy | B60N 2/2812 | 297/483 |
| 2014/0345625 | A1 * | 11/2014 | Abdoli-Eramaki | A61F 5/37 | 128/845 |
| 2015/0069813 | A1 * | 3/2015 | Furr | B60R 22/00 | 297/484 |
| 2015/0307061 | A1 * | 10/2015 | Chekaev | B60R 22/12 | 297/483 |
| 2016/0000631 | A1 | 1/2016 | Becker | | |
| 2018/0022312 | A1 * | 1/2018 | Roychoudhury | B60R 22/34 | 297/474 |
| 2020/0237474 | A1 * | 7/2020 | Muller | A61B 90/60 | |
| 2024/0398504 | A1 * | 12/2024 | Hellstern | A61B 90/60 | |
| 2025/0221791 | A1 * | 7/2025 | Hellstern | A61B 90/60 | |

FOREIGN PATENT DOCUMENTS

| | | | | |
|---|---|---|---|---|
| DE | 102020103861 | B3 | 4/2021 | |
| EP | 0335992 | A1 | 10/1989 | |
| EP | 0361369 | A2 | 4/1990 | |
| EP | 3117814 | A1 | 1/2017 | |
| GB | 2260687 | A * | 4/1993 | A47D 13/025 |
| JP | 2007519428 | A | 7/2007 | |

OTHER PUBLICATIONS

German Office Action for corresponding DE Application No. 10 2021 125 480.9; Mailing Date, Jun. 9, 2022.

International Search Report corresponding to International Application No. PCT/EP2022/076253; Mailing Date, Jan. 24, 2023.

Written Opinion corresponding to International Application No. PCT/EP2022/076253; Mailing Date, Jan. 24, 2023.

JPO Notice of Reasons for Refusal corresponding to JP Application No. 2024-518458; Issue date, Jun. 29, 2026, 9 pages.

* cited by examiner

SYSTEM FOR SUPPORTING A SURGEON

CROSS REFERENCE TO RELATED APPLICATIONS

This application is a National Stage of PCT Application No. PCT/EP2022/076253 filed on Sep. 21, 2022, which claims priority to German Patent Application No. 10 2021 125 480.9 filed on Sep. 30, 2021, the contents each of which are incorporated herein by reference thereto.

TECHNICAL FIELD

The present disclosure relates to a system for supporting a surgeon in surgery as well as, for example, laboratory personnel or dentists.

BACKGROUND

Supporting systems for surgeons are generally known and serve to support the surgeon normally standing at the operation table in such way that he or she can perform operations, sometimes of long duration, operations in a forced position or operations in special demands on the surgeon's fine motor skills with little or no fatigue, and, ideally, can perform them reliably and to a high quality.

For this purpose, DE 10 2020 103 861 B3 discloses an operating chair which serves to support a surgeon. The operating chair has a seat supported by a height-adjustable column, the column standing on a joint device which defines two tilt axes for the column and to which a locking device is assigned in order to lock manually set tilt positions so that the column maintains a desired tilt position. The operating chair can also have a pelvic support and an abdominal support, which provides the surgeon with good support, particularly in the case of highly inclined sitting positions.

In addition, U.S. Pat. No. 3,754,787 describes an operating chair which has a seat supported by a central column with a height- and tilt-adjustable chest support which protrudes from the front of the seat so that the surgeon can lean his chest against the chest support. The chest support supports the surgeon's upper body.

US 2016/0000631 A1 proposes an operating chair with a seat supported by a column, in which, among other things, a chest support protruding from the front of the seat has several adjustable support pads. The chest support can be adjusted in order to achieve the most ergonomic sitting position possible for the surgeon.

However, the use of an abdominal or chest support can lead to an unpleasant sensation of pressure in the surgeon's chest and/or abdominal area. Furthermore, the chest support restricts the surgeon's natural breathing movements somewhat. The chest support also transfers the surgeon's breathing movements to his upper body, which means that the surgeon has to compensate for these breathing movements with his arms during the operation. This leads to the surgeon tiring more quickly, particularly during lengthy operations.

U.S. Pat. No. 6,224,154 B1 discloses an operating chair having a main column to which a tiltable seat and an anchorage for a harness are attached. The harness has two shoulder straps which meet at a suspension point in the back area of the surgeon. In one embodiment, the harness also has straps in the crotch area of the surgeon (so-called leg loops), which are particularly uncomfortable during lengthy operations. The leg loops also make it more difficult to put on the harness. The leg loops can cause unpleasant pressure points for the surgeon, especially when seated. The suspension point of the harness is connected to the anchorage on the column via a chain.

BRIEF SUMMARY

Based on this, it is an objective of the present disclosure to create an improved system for supporting the surgeon, in which improved support of the surgeon's upper body is achieved and, in addition, the wearing comfort for the surgeon is increased.

Disclosed is a system for supporting a surgeon, including: an operating chair with a base frame which can be placed on a floor, with a seat for the surgeon supported on the base frame; and a restraining device for the surgeon, having a harness system which has at least a first and a second restraining belt which are connected to at least a first suspension point and a second suspension point of a traction device, the first suspension point being spaced-apart from the second suspension point, wherein the traction device is arranged to set a distance between the first suspension point and the second suspension point.

The system according to the present disclosure has an operating chair and a restraining device for the surgeon. The operating chair has a base frame, which can be placed on the floor, and a seat for the surgeon supported on the base frame. The restraining device has a harness system comprising at least a first and a second restraining harness, which are connected to at least a first and a second spaced-apart suspension point of a traction device. The traction device is configured to define (fix) the distance between the suspension points and in any case to resist a reduction in distance.

This prevents the individual restraining harnesses from contracting (constricting) when the harness system is under tensile load, which is perceived as uncomfortable by the surgeon. Preventing the restraining harnesses from constricting increases the surgeon's comfort, which may, for example, prevent increased pauses during surgery and/or losses of surgeon's operating quality. In addition, the harness system relieves the surgeon's back, lumbar and neck muscles. Furthermore, the system according to the present disclosure improves the surgeon's freedom of movement compared to conventional systems with abdominal and/or chest supports, whereby the surgeon is able to follow his usual work and movement sequence. The traction device can preferably be configured such that the positioning of the suspension points is adjustable or adaptable relative to each other, whereby the traction device (as well as the harness system, which is connected to the traction device at the suspension points) can be adapted to the length of the surgeon's upper body. This leads to an improvement in force transmissions and reliefs. In particular, the position of the suspension points can be adjusted stepless or with locking points.

An important aspect of the system according to the present disclosure is the traction device with which the distance between the suspension points, to which the at least one first restraining harness and the at least one second restraining harness of the harness system are connected, is fixedly defined. The distance between the suspension points remains at least substantially the same even when the harness system is under tensile load. The system according to the present disclosure prevents the harness from constricting and causing the surgeon to feel unpleasant and undesirable pressure in the upper body area. This increases wearing comfort for the surgeon.

Furthermore, in the system according to the present disclosure, the upper body of the surgeon is held in a desired inclined position by the traction device to which the harness system is connected at the suspension points and which can exert a tensile force on the upper body of the surgeon via the harness system. As a result, the restraining device provides the surgeon with secure support for the upper body and at the same time leaves the necessary freedom of movement.

In the system according to the present disclosure, the surgeon can also sit on the operating chair, whereby his upper body can be held in a desired position by the restraining device, as described above, with the harness system and the traction device thereby relieving the strain. In particular, this can prevent an undesirable feeling of pressure in the surgeon's abdominal area. In particular, the support close to the shoulder supports, in particular steady fine motor work while preventing blood and/or lymph congestion, which can lead to discomfort in the surgeon's arms.

In a suspension point, which is understood to be a point at which a restraining harness of the harness system is connected to the traction device, the restraining harness can be attached to the traction device or can also be folded over, for example through an eyelet.

Preferably, the harness system further comprises the following:

A first shoulder strap connected to a first upper suspension point and to a first lower suspension point of the traction device spaced therefrom, and a second shoulder strap connected to a second upper suspension point and to a second lower suspension point of the traction device spaced therefrom.

The shoulder straps allow the surgeon to breathe freely without an uncomfortable feeling of pressure in the chest area and without the breathing movements being transferred to the surgeon's body. In addition, the surgeon is held securely in the desired position. In particular, the shoulder straps can be padded to further increase the surgeon's comfort. The shoulder straps are preferably adjustable in length so that they can be adapted to the height of the surgeon.

It is preferred that the harness system comprises a waist strap connected to the lower suspension points, the shoulder straps or to lower regions of the shoulder straps.

In particular, the waist strap can be worn below the surgeon's abdomen. The waist strap provides the surgeon with additional safety without restricting his breathing movements, for example in the abdominal area. In addition, padding located in the lower back area of the surgeon can be attached to the support element (a lordosis support), which supports the lordosis (curvature) of the surgeon's spine.

It is also possible for the waist strap to be connected to the traction device via the lower suspension points, with the first shoulder strap being connected to the first upper suspension point and to the waist strap, for example to a front side of the waist strap, and the second shoulder strap being connected to the second upper suspension point and to the waist strap, for example to a front side of the waist strap.

In a preferred embodiment, the traction device has at least a first dimensionally stable support element which bridges the distance between the first and second suspension points. The support element can, for example, be designed as a bending beam, which is configured to be resistant to bending or torsion.

In addition, the support element can also be designed as a support plate or a skeletonized plate. The skeletonized plate can, for example, be manufactured using an additive manufacturing process, which enables the skeletonized plate to be shaped in such a way that it is optimized to keep the distance between the two suspension points constant even under tensile load at the suspension points. This can be achieved, for example, by a structure that is as rigid as possible in a direction of the tensioning points pointing towards each other.

The first support element can, for example, be made at least partially from a metal, an alloy, a light metal, a dimensionally stable plastic and/or a composite material.

The distance between the upper suspension points can be defined and bridged particularly easily by the first dimensionally stable support element.

In a preferred embodiment, the traction device has a further dimensionally stable support element, which defines the distance between the lower suspension points at which the harness system is connected to the traction device and bridges this distance.

The further support element can preferably be constructed in the same way as the first support element described above.

The distance between the lower suspension points can be defined and fixed by the second support element, so that constriction of the shoulder straps in a lower region can be prevented.

Preferably, the first support element and the second support element form a support unit, for example, in single-piece (monolithic) which defines and bridges a distance between the first upper suspension point and the first lower suspension point as well as a distance between the second upper suspension point and the second lower suspension point.

The support unit formed from the support elements can prevent the individual shoulder straps from constricting and the waist strap from slipping, which can increase the wearing comfort for the surgeon. The support unit preferably has an adjusting device with which the positioning of the suspension points relative to each other can be adjusted. This allows the support unit to be adapted to the length of the surgeon's upper body. This leads to an improvement in the transmission of the holding force to the surgeon's body and thus to his or her relief. In particular, the adjusting device can enable stepless positioning of the suspension points or positioning with locking points.

Preferably, a traction element connects the support unit to an abutment.

The abutment can be formed, for example, by an abutment column with at least one anchorage for the traction element. The abutment column can be attached to the operating chair so that the abutment column is also pivoted when the operating chair is pivoted. For example, the abutment column can be attached to the operating chair in such a way that it moves the abutment column when the seat height of the seat is adjusted. As a result, the distance between the seat and the abutment column remains the same even when the seat height is adjusted.

It is also possible that the abutment column is attached to the base frame of the operating chair, so that the abutment column is not pivoted when the operating chair is pivoted. Also, a distance between the seat and the abutment column does not remain constant when the seat height of the seat is adjusted, but changes.

Tensile forces can be transferred to the abutment because the support unit is connected to an abutment via the traction element.

A traction element can be understood to be, for example, a belt, a strap, a chain or a band. The abutment can form a fixed point which fixes the support unit via the traction element in the tensile direction under tensile load, without restricting movement of the support unit in the lateral direction.

Preferably, the support unit has a connecting device which is configured to variably define a connection point at which the traction element is connected to the support unit.

The point at which the traction element holds back (restrains) the upper body of the surgeon can be varied by the connecting device, whereby the restraining device can be adapted to the size of the surgeon. The connecting device can, for example, be formed by a movable and lockable eyelet into which a hook (e.g. a snap hook or a safety hook) or a shackle (e.g. a safety shackle) can be hooked. By using a safety shackle with a so-called panic lock, the surgeon can be quickly and safely separated from the restraining device.

In a further embodiment example, a first support element is assigned a first traction element that connects the first support element to a first abutment and the second support element is assigned a second traction element that connects the second support element to a second abutment, wherein the first abutment and the second abutment are preferably configured to variably determine the positions of the respective abutments at which the respective traction elements are attached to the abutments.

By using two abutments, each associated with a support element, the surgeon's upper body can be held back (restrained) at two (different) points that can be adjusted independently of each other. This enables improved support of the surgeon's upper body.

Preferably, the abutment has a height-adjustable and/or laterally adjustable anchorage. An embodiment in which the anchorage is height-adjustable is preferred.

If the second support element is connected to a separate abutment via a separate second traction element, the second abutment preferably has a height-adjustable and/or laterally adjustable anchorage. Here too, it is preferred that the anchorage is only height-adjustable.

In particular, the abutment has a height-adjustable and/or laterally adjustable winch. A height-adjustable winch is preferred. The winch is a particularly simple way of variably defining (adjusting) a length of the traction element. The length of the traction element can be used to set the angle of inclination of the upper body at which the restraining device restrains the upper body of the surgeon.

It is preferred that the abutment has a winch and a height-adjustable deflecting device, for example, with a height-adjustable guide roller. The deflecting device makes it possible to attach the winch to a rear side of the abutment. The abutment can, for example, have a support column to the rear of which the winch can be attached. This can provide sufficient space for the surgeon between the abutment and the operating chair so that the surgeon can sit upright comfortably without being restricted in his back by the winch. Alternatively, however, the winch can also be attached to the front of the abutment.

In particular, the winch has at least one electric geared motor for driving a winding body, the geared motor preferably being of self-locking design. The length of the traction element can be changed (adjusted) by the electric geared motor.

Preferably, the operating chair has a height-adjustable column, at the upper end of which the seat is inclinably arranged. The height-adjustable column of the operating chair is attached to a base frame.

The height-adjustable column allows the surgeon to adjust his or her sitting position.

In particular, the operating chair has a joint device at the lower end of the height-adjustable column, which fixes only one pivot axis. The operating chair is thus designed to be laterally pivotable.

BRIEF DESCRIPTION OF THE DRAWINGS

Further details of advantageous further embodiments or details of the present disclosure are apparent from the drawings, the description and the claims. The drawings show the following:

DETAILED DESCRIPTION

Figure 1:
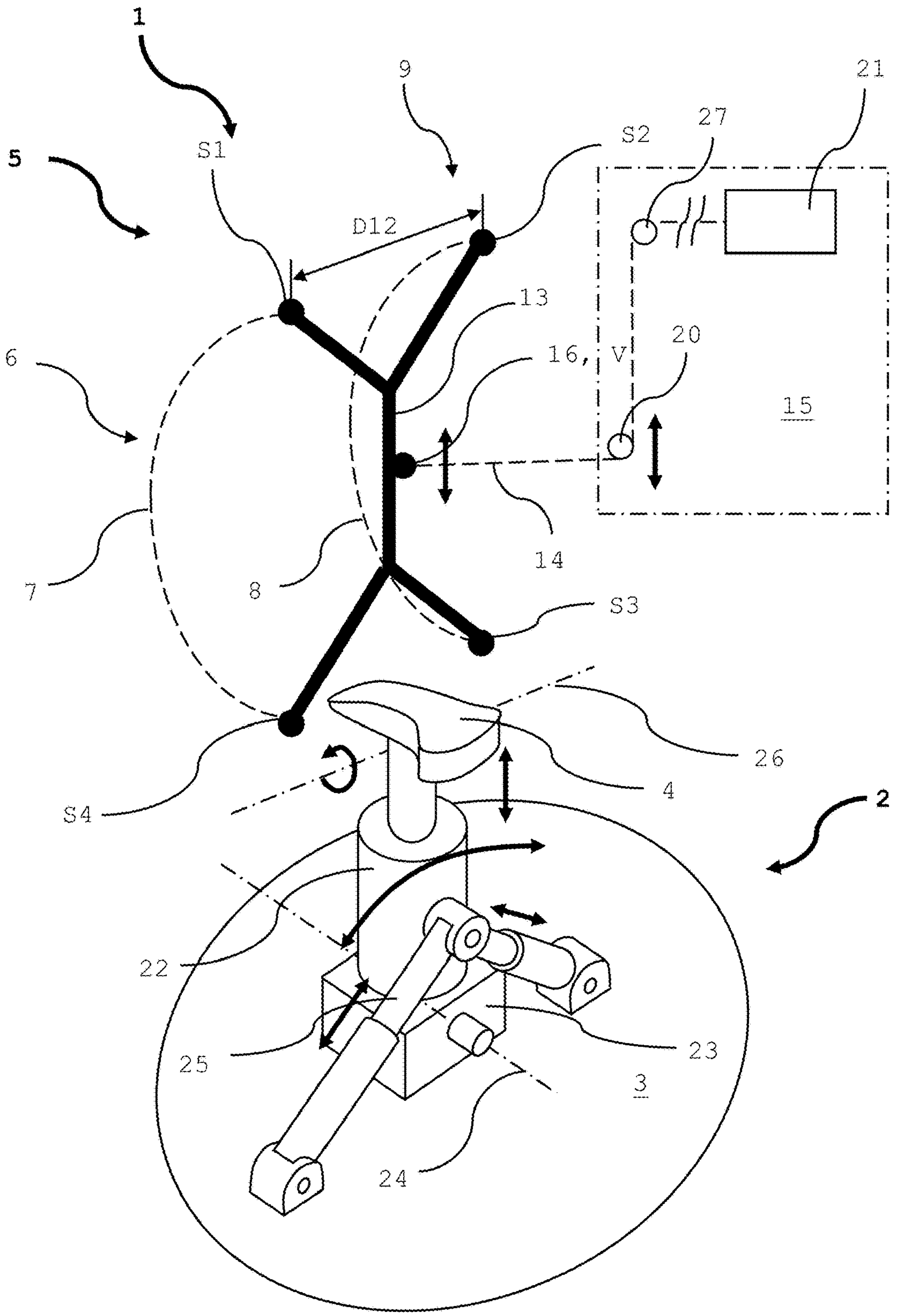
FIG. 1 a simplified perspective view of an embodiment example of the system for supporting a surgeon according to the present disclosure, FIG. 2 a simplified perspective view of a further embodiment example of the system according to the present disclosure for supporting a surgeon, FIGS. 3*a* to 3*g* a plan and simplified view of different embodiment examples of the support unit, FIGS. 4*a* and 4*b* a perspective view of different embodiment examples of the harness system, FIG. 5 a simplified side view of an embodiment example of the system according to the present disclosure for supporting a surgeon, FIG. 6 a schematic side view of a modified embodiment example of the system according to the present disclosure for supporting a surgeon.

FIG. 1 illustrates a system 1 which serves to support an operator, such as a surgeon, in his or her work on the patient, in particular in his work on the operating table.

The system 1 has an operating chair 2 and a restraining device 5. The operating chair 2 has a base frame 3 which can be placed on the floor. A pivotable column 22 is arranged on the base frame 3. The column 22 is height-adjustable, for example by means of a servomotor. The height-adjustable column 22 is connected to the base frame 3 via a joint device 23. The joint device 23 defines a pivot axis 24 about which the operating chair 2 can be pivoted sideways. Furthermore, a pivot device 25 is arranged on the operating chair 2, with which a pivot movement of the operating chair 2 can be supported. The pivot device 25 can, for example, be actively controlled by an electric motor. A seat 4 is arranged at the upper end of the height-adjustable column 22. The seat 4 can be inclined forwards and backwards about an inclination axis 26.

The restraining device 5 for the surgeon comprises a harness system 6 and a traction device 9. In the illustrated embodiment example, the harness system comprises a first shoulder strap 7 and a second shoulder strap 8. The harness system 6 is connected to the traction device 9 at the suspension points S1, S2, S3 and S4 (attached to it).

In the embodiment example illustrated in FIG. 1, a support unit 13 defines the distance D12 between the first upper suspension point S1 and the second upper suspension point S2 and bridges this distance D12.

The support unit 13 also determines the distance D23 between the second lower suspension point S3 and the first lower suspension point S4. The support unit 13 can, for example, be configured as a (rigid, dimensionally stable) frame. The support unit 13 can also be configured as a closed plate or a plate provided with openings or as a skeletonized plate, in each case made of metal or plastic.

The support unit 13 is connected to an abutment 15 via a traction element 14. The support unit 13 also has a height-adjustable connecting device 16, with which it is possible to variably define a connection point V between the traction element 14 and the support unit 13. This allows the support unit 13 and the connection point V to be adapted to the height of the surgeon. The abutment 15 comprises a height-adjustable deflection roller 20 and further deflection rollers 27, with which the traction element 14 is guided to a winch which has an electric geared motor 21, which can be designed to be self-locking (self-braking), for example.

Figure 2:
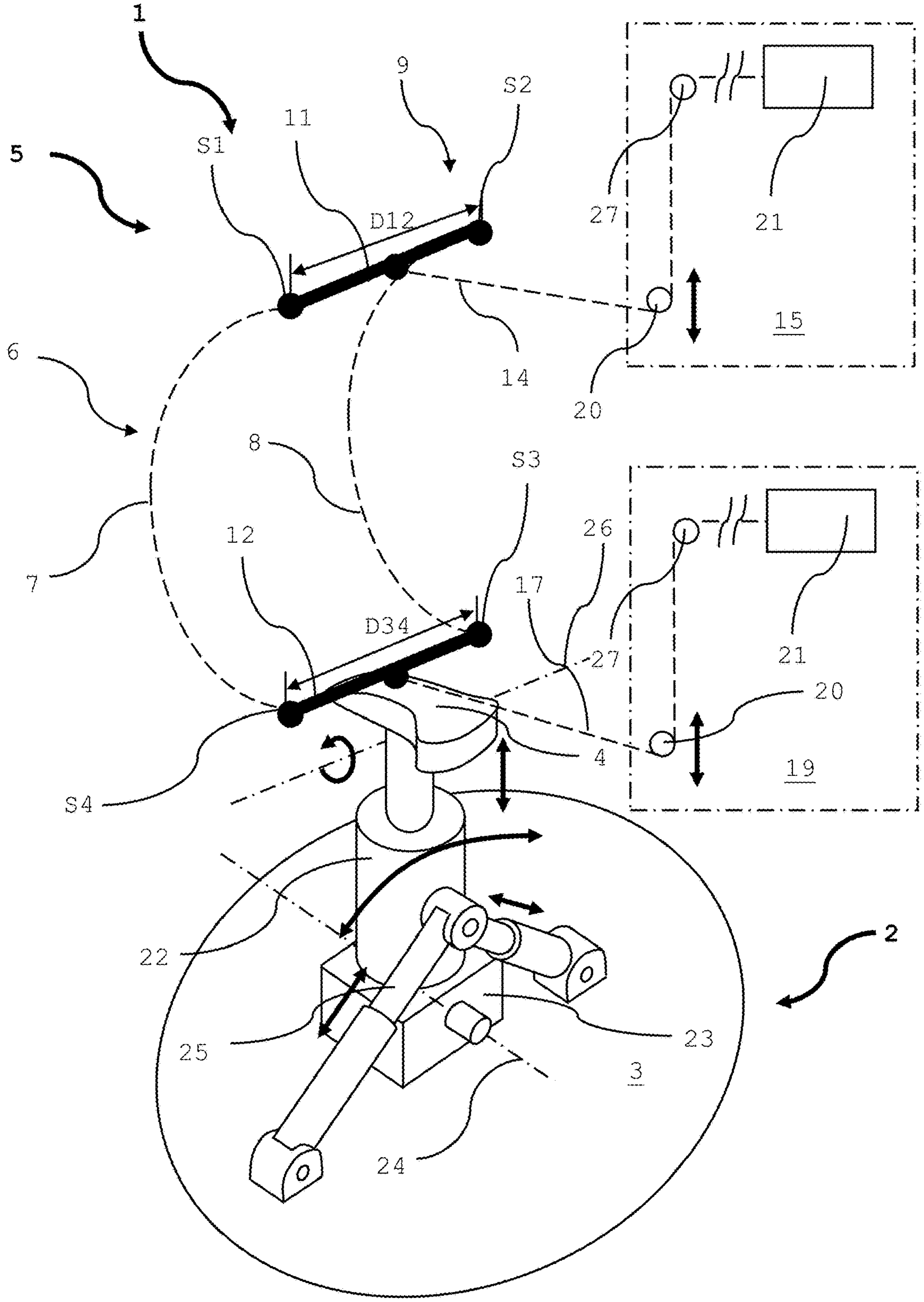

FIG. 2 illustrates an alternative embodiment example of system 1 according to the present disclosure. In FIG. 2, a first support element 11 bridges the distance D12 between the upper suspension points S1 and S2. A second support element 12 bridges the distance D34 between the lower suspension points S3 and S4. In this example, the first and second support elements 11, 12 do not form a single-piece support unit 13. The first support element 11 is mechanically connected to a first abutment 15 via a first traction element 14. The second support element 12 is mechanically connected to a second abutment 19 via a second traction element 17. In this example, the abutments 15, 19 each have a height-adjustable deflection roller, at least one further (non-height-adjustable) deflection roller 27 and an electric geared motor. The abutments can be constructed identically.

Figure 3A:
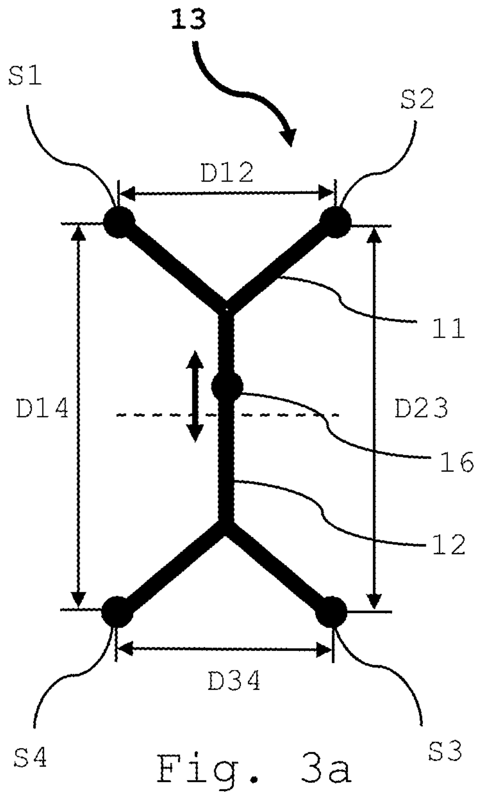

FIG. 3*a* shows an exemplary support unit 13. The support unit 13 has a first upper suspension point S1, a second upper suspension point S2, a first lower suspension point S4 and a second lower suspension point S3.

The support unit 13 comprises a first support element 11 and a second support element 12. The first support element 11 is configured as a star-shaped rigid element, which has three legs. Two upper legs of the first support element 11 lead to the first upper suspension points S1 and S2.

The second support element 12 is also designed as a three-legged star, with the lower two legs of the second support element 12 leading to the lower suspension points S3 and S4.

The third leg of the first support element 11 and the second support element 12 meet in the middle and are connected in such a way that they form a single-piece (monolithic) unit.

The support unit 13 bridges the distance D12 between the first upper suspension point S1 and the second upper suspension point S2, the distance D23 between the second upper suspension point S2 and the second lower suspension point S3, the distance D34 between the second lower suspension point S3 and the first lower suspension point S4, and the distance D14 between the first upper suspension point S1 and the first lower suspension point S4. The support unit 13 is designed as a rigid frame. Furthermore, the support unit 13 has a height-adjustable connecting device 16, to which a traction element 14 can be connected.

Figure 3B:
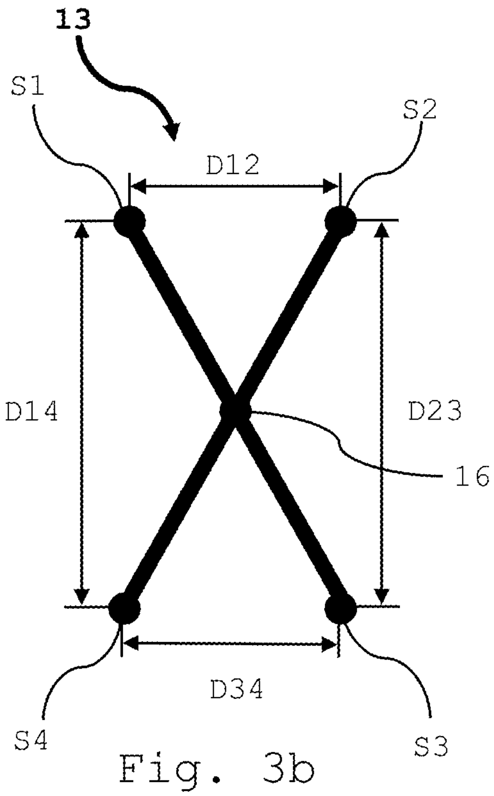

FIG. 3*b* shows a further example of a support unit 13. In this embodiment example, the support unit 13 is at least essentially X-shaped so that the distances D12, D23, D34 and D14 are also bridged by the support unit 13. In this example, the connecting device 16 is arranged at the intersection of the X-shaped support unit 13.

Figure 3C:
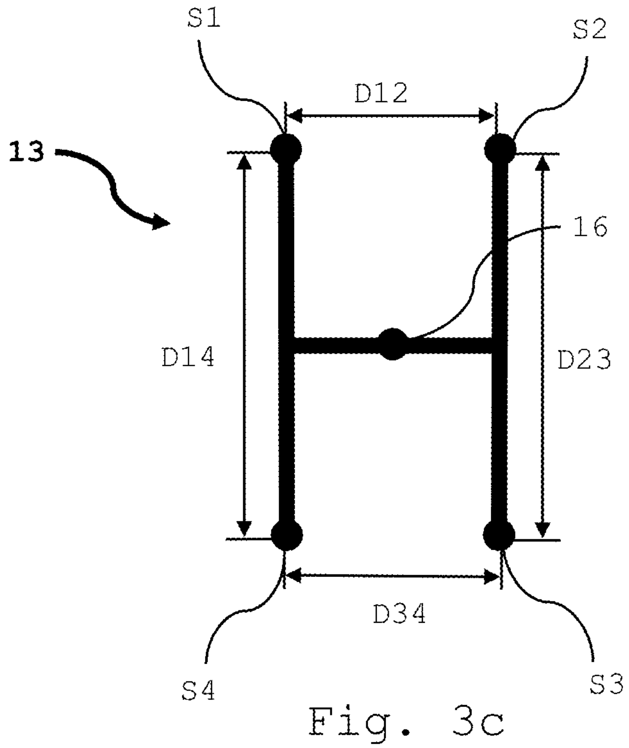

FIG. 3*c* shows an example of a support unit in which the support unit 13 is at least essentially H-shaped. In this embodiment example, the support unit 13 also bridges the distances D12, D23, D34 and D14. In addition, the support unit 13 has a connecting device 16, which is preferably attached in a central area of the H-shaped support unit 13.

Figure 3D:
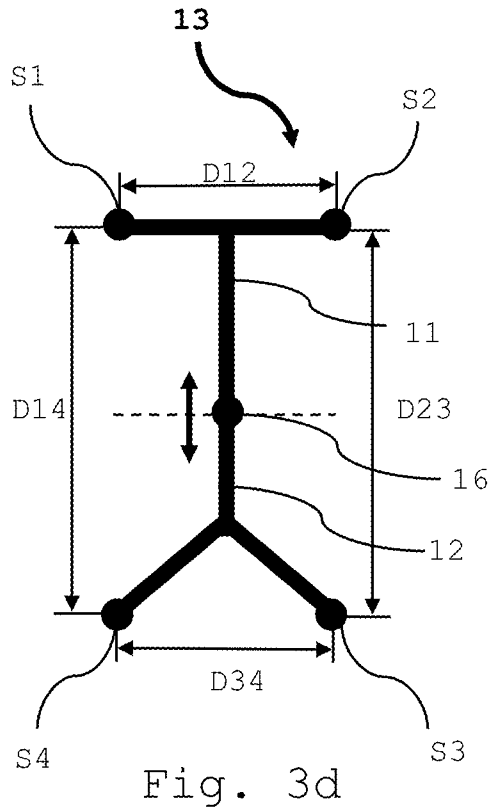

FIG. 3*d* shows a further example of the support unit 13. In this example, the first support element 11 has at least essentially a T-shape and the second support element 12 has a three-legged star shape. In this embodiment example, the first support element 11 and the second support element 12 are connected to form a support unit 13. The connecting device 16 is attached to the support unit 13, preferably in an area in which the legs of the support elements 11, 12 are connected to one another. The connecting device 16 can be height-adjustable.

Figure 3E:
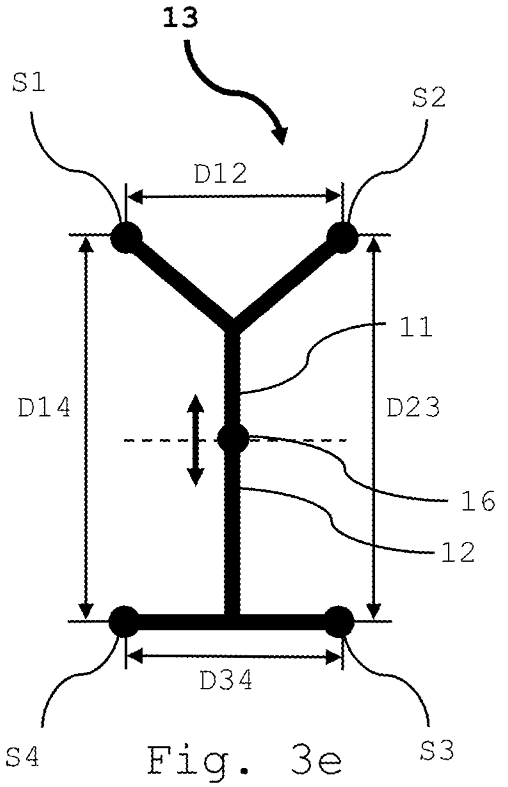

FIG. 3*e* shows a support unit 13 in which the first support element 11 is designed as a three-legged star and the second support element 12 is designed as a T-shaped element. In this example too, as in the example in FIG. 3*d*, a height-adjustable connecting device 16 is attached to the support unit 13.

Figure 3F:
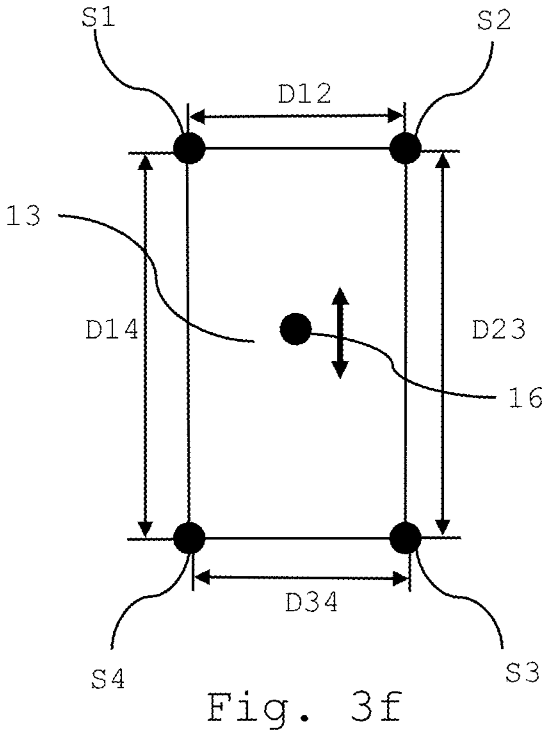

FIG. 3*f* illustrates an example of the support unit 13, in which the support unit 13 is designed as a plate. In this example, the height-adjustable connecting device 16 is mounted in a central area of the plate. It is also possible, as already described above, to use a skeletonized plate as support unit 13.

In the examples of the support unit 13 as illustrated in FIGS. 3*a* to 3*f*, the distances between the suspension points S1, S2, S3 and S4 of the support unit 13 are fixed. The distances also remain at least substantially the same during operation, i.e. under tensile load of the harness system 6.

Figure 3G:
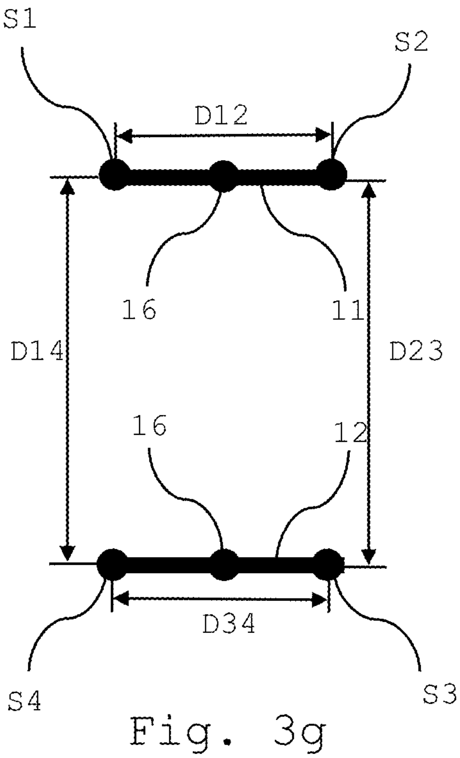

FIG. 3*g* shows an example of an alternative to the support unit 13. In this example, the upper suspension points S1 and S2 are bridged by a first support element 11. Furthermore, a second support element 12 bridges the lower suspension points S3 and S4. In this example, a connecting device 16 is attached to the first support element 11 and to the second support element.

The first support element 11 and the second support element 12 are not connected in this embodiment example. In this embodiment example, a first traction element 14 is associated with the first support element 11 and is (mechanically) connected to the connecting device 16 of the first support element 11. A second traction element 17 is associated with the second support element 12, which is (mechanically) connected to the connecting device 16 of the second support element 12. In this embodiment, the support elements 11 and 12 can be connected to separate abutments 15 and 19 via the traction elements 14 and 17.

Figure 4A:
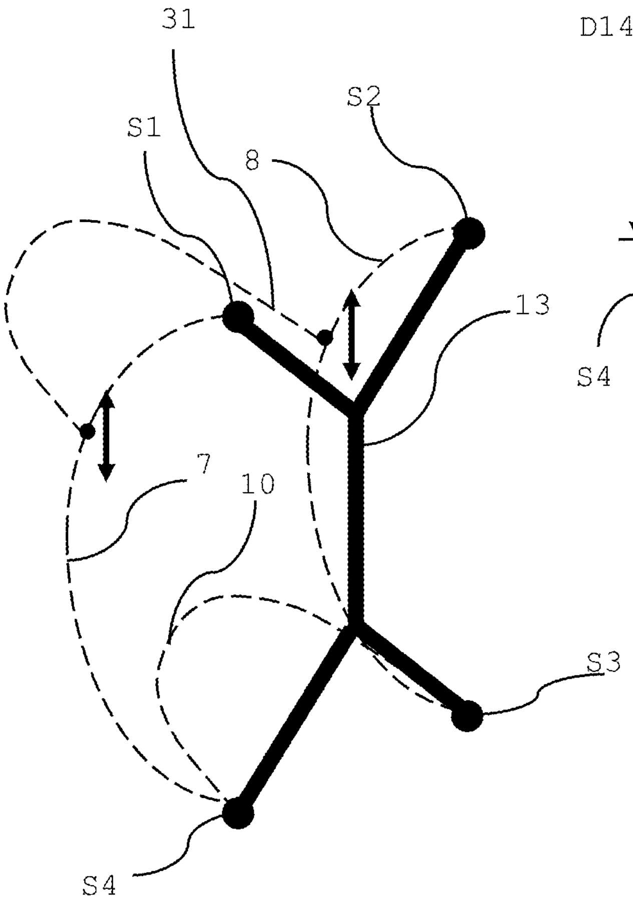

FIG. 4*a* shows an embodiment example of the harness system 6. In this embodiment example, the harness system 6 comprises a first shoulder strap 7, a second shoulder strap 8 and a waist strap 10. The first shoulder strap 7 is attached to the first upper suspension point S1 and the first lower suspension point S4. The second shoulder strap 8 is attached to the second upper suspension point S2 and the second lower suspension point S3. The waist strap 10 is attached to the lower suspension points S3 and S4. In FIG. 4*a*, a chest strap 31 is attached with one end to the first shoulder strap 7 and with the other end to the second shoulder strap 8. In this example, the chest strap 31 mechanically connects the shoulder straps 7, 8. The points at which the chest strap 31 is connected to the shoulder straps 7, 8 can be continuously displaced and locked along the shoulder straps 7, 8 (as illustrated by the double arrows in FIG. 4*a*). In addition, the chest strap 31 is preferably continuously adjustable in length. When the harness 10 is put on by a surgeon, the chest strap 31 can be adjusted so that it extends at the surgeon's chest height. As a result, the shoulder straps 7, 8 are held in positions that are comfortable for the surgeon, so that the surgeon does not experience any incisions, lymph congestion and/or discomfort in his arms.

Figure 4B:
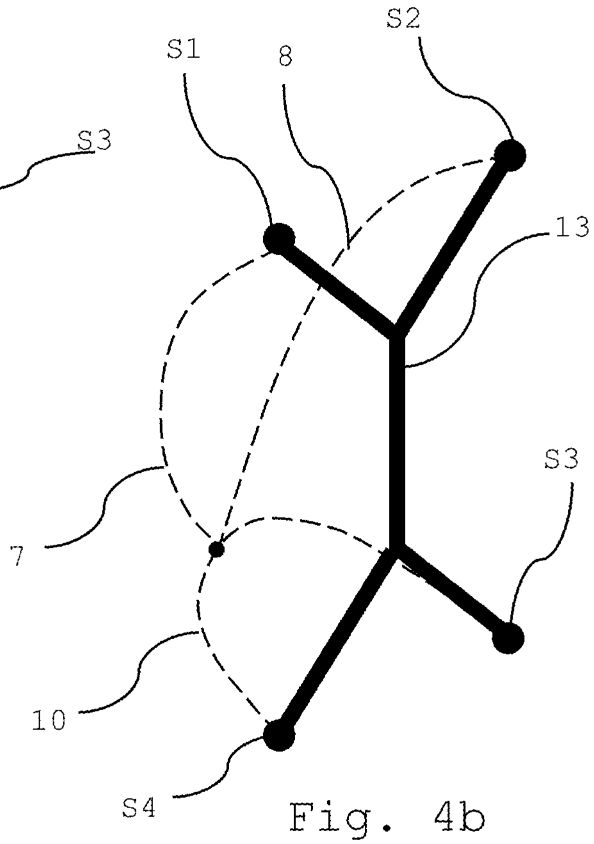

FIG. 4*b* shows a further embodiment example of the harness system 6. In this embodiment example, the first shoulder strap 7 and the second shoulder strap 8 are not attached to the lower suspension straps, but to the waist strap 10. The waist strap 10 is in turn attached to the lower suspension points S3 and S4.

Figure 5:
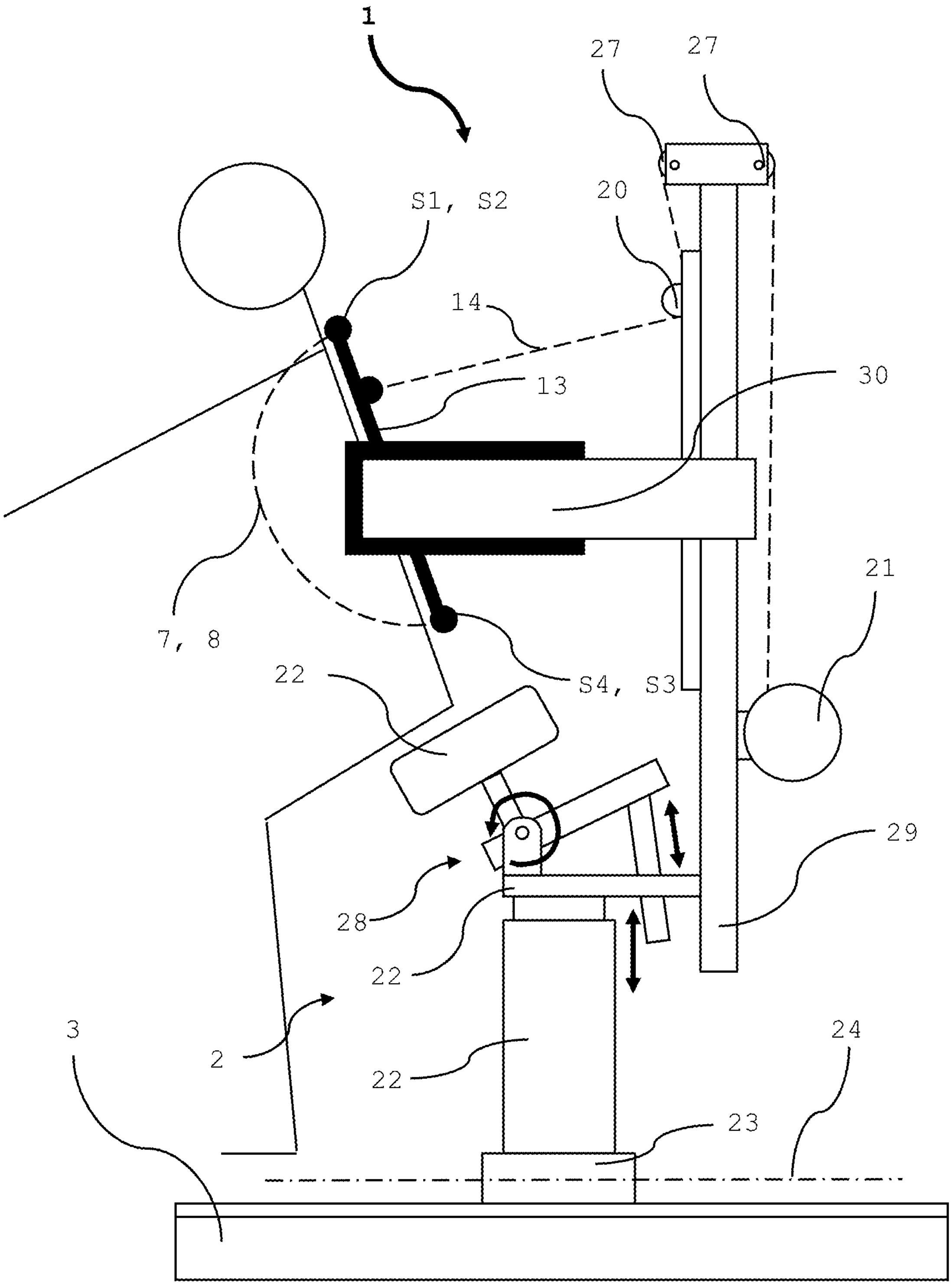

FIG. 5 shows an embodiment example of the system according to the present disclosure. The system 1 comprises a base frame 3, on which a height-adjustable column 22 is arranged, which is configured to be pivotable via a joint device 23. The joint device 23 defines a pivot axis 24.

An inclination device 28 is arranged at the upper end of the column 22, with which the seat 22 can be inclined forwards or backwards. The inclination device 28 can be actuated by the surgeon manually and/or by motor, for example via an operating device.

Furthermore, an abutment column 29 is attached (mounted) to the column 22. The abutment column 29 is firmly connected to the column 22 of the operating chair 2, so that it pivots with the operating chair when the operating chair 2 is pivoted sideways.

Deflection rollers 27 are arranged at the upper end of the abutment column 29 with which the traction element 14 is deflected from the front side of the abutment column 29 to the rear side of the abutment column 29. The traction element 14 is, thus, guided to a winch with an electric geared motor 21, which can be designed to be self-locking.

A height-adjustable guide roller 20 is arranged at the front of the abutment column 29. The traction element 14 is connected to a support element 13, which a surgeon can carry on his or her back. The restraining harnesses 7, 8 of the harness system 6 are connected to the support unit 13 at the suspension points S1 to S4.

In the present embodiment example, the first shoulder strap 7, which is connected to the first upper suspension point S1 and the second lower suspension point S4, is illustrated. Arm supports 30 are attached to the abutment column 29, which extend laterally next to the surgeon above the operating chair 2. An operating unit for the system 1 can be accommodated in the arm supports 30, for example.

Figure 6:
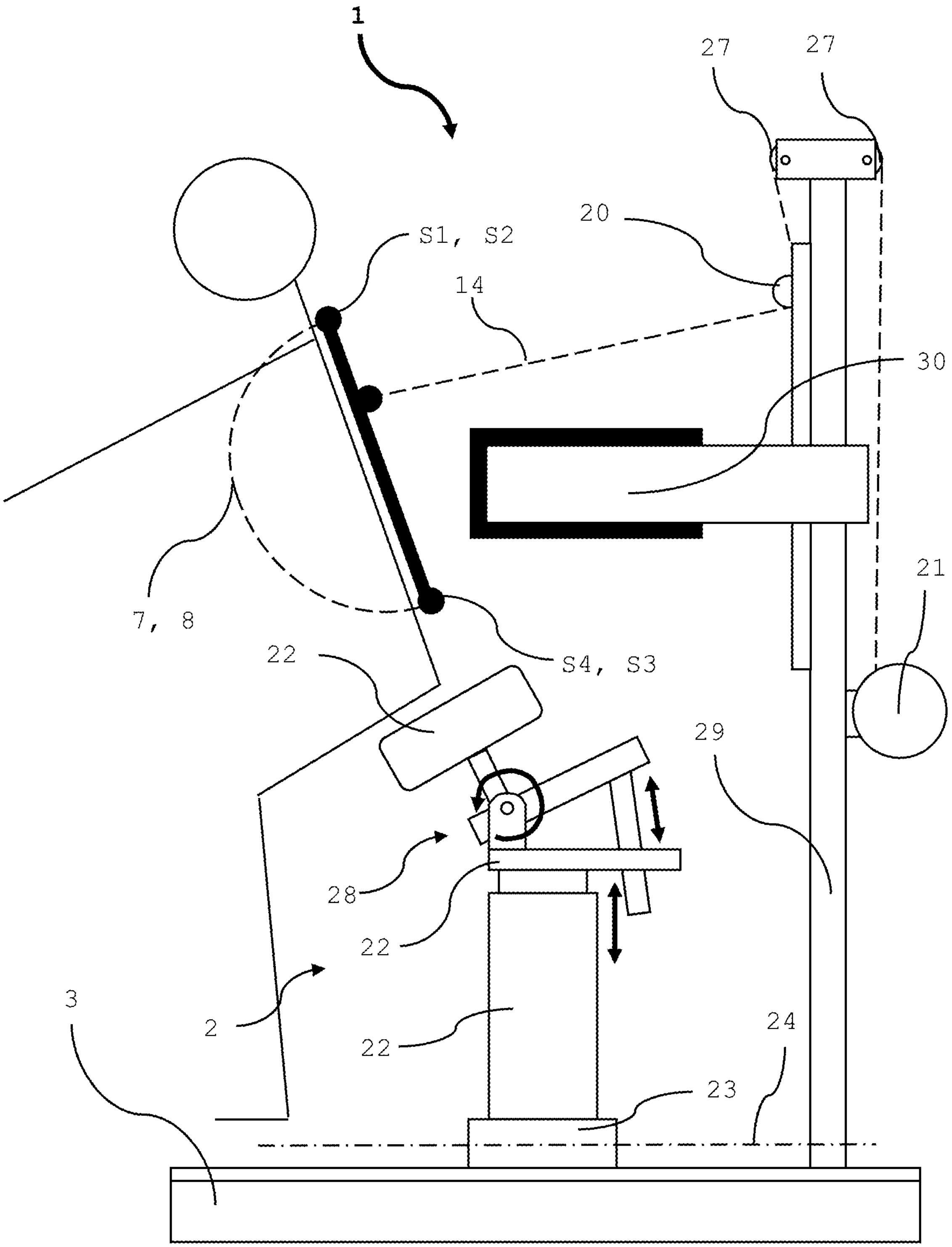

FIG. 6 illustrates a further embodiment example of the system 1. In this embodiment example, the abutment column 29 is rigidly connected to the base frame 3, for example with the column 22 can be inclined laterally as described above. In this case, the upper body of the surgeon is suspended in a pivoting manner by the traction element and can follow the lateral inclination. However, it is also possible to provide the support column 29 with its own inclination device so that the support column can be inclined independently of the column 22. A motorized adjusting device can be assigned to the inclination device. This can be designed with one or two axes in order to be able to tilt the abutment column forwards/backwards and/or sideways. In this way the operating chair 2 can be pivoted sideways manually or by motor independently of the abutment column 29.

The system 1 described in this respect for supporting the surgeon works as follows:

To perform an operation, the system 1 is moved to the operating table in a controlled manner by means of a controlled unit not shown further, wherein the control unit may, for example, have at least one joystick and further control buttons or other operating elements. The surgeon puts on the harness system 6 by slipping the at least two shoulder straps 7, 8 over his shoulders. If the harness system 6 has a waist strap 10, the surgeon puts on the waist strap 10 which, when put on, preferably extends in the lower abdominal region of the surgeon, preferably below his diaphragm or his ribcage. The surgeon can wear the harness system over his surgical gown as well as over or under additional surgical clothing, such as an X-ray apron. The surgeon is then dressed in sterile clothing, for example a sterile surgical gown. The surgeon can now enter the operating room, enter system 1 and be connected to the traction element 14 at his back by means of the connection unit 16 (the shackle or the carabiner hook), for example through a slit in the sterile surgical gown.

If the restraining device 5 has a support unit 13 as shown in FIG. 1, 3*a* to 3*f*, 4*a*, 4*b*, 5 or 6, the support unit 13 rests against the back of the surgeon in the applied state, so that the upper suspension points S1, S2 are arranged in the upper back region of the surgeon above the shoulders. The lower suspension points S3, S4 are arranged in the lower back area, for example in the lumbar vertebrae area of the surgeon. The distance D14, D23 between the upper suspension points S1, S2 and the lower suspension points S3, S4 can be variably adapted to the length of the surgeon's back.

If the restraining device 5 has two unconnected support elements 11, 12, the first support element 11 rests on the upper back area of the surgeon when it is in the applied state and the second support element 12 rests on the lower back region of the surgeon.

The surgeon then takes a seat on the seat 4 of the operating chair 2. The support unit 13 can be connected to the abutment 15 via the traction element 14 before the surgeon puts on the harness system 6. The harness system 6 can also be applied by the surgeon first. The support unit 13 is then connected to the traction element 14 via the connection unit 16. The traction element 14 is not under tensile stress when the surgeon applies the harness system 6 and/or when the support unit 13 is connected to the traction element 14 via the connecting device 16. The point on the connecting device 16 can now be adapted to the size of the surgeon to provide comfortable restraint for the surgeon. For example, this point can be located in the area between the shoulder blades of the surgeon.

The surgeon can now use the control unit to shorten the length of the traction element 14 so that he can lean forward into the harness system 6 and is held back by the traction device 9 at a desired angle of inclination of his upper body. The traction element 14 and the harness system 6 are now under tensile load. By changing the length of the traction element 14, the surgeon can also freely choose the angle of inclination at which he is supported by the traction device 9 during the operation. The surgeon can also move his upper body laterally, whereby the connection point V, at which the traction element 14 is connected to the support unit 13 via the connection unit 16, describes an arc of a circle with the abutment column 29 as the center when the upper body moves laterally.

In addition, the surgeon can use the control unit to set a desired height of the operating chair 2, a desired lateral inclination of the operating chair 2 and a desired inclination of the seat 4. If a lateral angle of inclination of the abutment column 29 can be set independently of the angle of inclination of the operating chair 2, i.e. the abutment column 29 is not firmly fixed to the column 22 of the operating chair 2, the surgeon can set the angle of inclination of the abutment column 29 independently.

Furthermore, a second control unit can be provided with which it is possible for a further person to control the system 1, for example by the person making the desired settings on the operating chair 2 and/or traction device 9 at the instruction of the surgeon.

The system according to the present disclosure is used to assist a surgeon. It has an operating chair 2 and a restraining device 5 for the surgeon. The restraining device 5 has a harness system 6 which comprises at least a first and a second restraining harness 7, 8 which are connected to at least a first and a second spaced-apart tension point S1, S2, S3, S4 of a traction device 9, wherein the traction device 9 is configured to determine the distance between the suspension points S1, S2, S3, S4 and in any case to resist a change in distance. The system according to the present disclosure improves the wearing comfort of the restraining device 5 for the surgeon, since it prevents the restraining harnesses 7, 8 of the harness system 6 from constricting under tensile load, which can lead to unpleasant and undesirable pressure sensations in the upper body area of the surgeon.

REFERENCE SIGN

1 system for supporting a surgeon
2 operating chair
3 base frame
4 seat
5 restraining device
6 harness system
7 first restraining harness (first shoulder strap)
8 second restraining harness (second shoulder strap)
9 traction device
10 waist strap
11 first support element
12 second support element
13 support unit
14 (first) traction element
15 (first) abutment
16 connecting device
17 (second) traction element
18 (second) support element
19 (second) abutment
20 deflecting device
21 electric geared motor
22 column of the operating chair
23 joint device
24 pivot axis
25 pivot device
26 inclination axis
27 further deflection rollers
28 inclination device
29 abutment column
30 arm support (lateral support)
31 chest strap
D12 distance between the upper suspension points
D23 distance between the second upper and the first lower suspension point
D34 distance between the lower suspension points
D14 distance between the first upper and the second lower suspension point
S1 first upper suspension point
S2 second upper suspension point
S3 second lower suspension point
S4 first lower suspension point
V connection point V

What is claimed is:

1. A system for supporting a surgeon, comprising:

an operating chair with a base frame which can be placed on a floor, with a seat for the surgeon supported on the base frame; and a restraining device for the surgeon, having a harness system which has at least a first and a second restraining belt which are connected to at least a first suspension point and a second suspension point of a traction device, the first suspension point being spaced-apart from the second suspension point, wherein the traction device is arranged to set a distance between the first suspension point and the second suspension point;

further comprising a support unit that defines and bridges a distance between the first suspension point and the second suspension point, the support unit configured to rest against the back of the surgeon;

wherein the support unit includes a connecting device configured to variably define a connection point at which the traction device is connected to the support unit via a traction element.

2. The system according to claim 1 wherein the harness system further comprises a first shoulder strap connected to a first upper suspension point and a first lower suspension point of the traction device at a distance from each other, and a second shoulder strap, which is connected to a second upper suspension point and a second lower suspension point of the traction device at a distance from one another.

3. The system according to claim 2, wherein the harness system has a waist strap which is connected to the first lower suspension point and the second lower suspension point on the traction device.

4. The system according to claim 3, wherein the support unit includes at least a first dimensionally stable support element which bridges the distance between the first and the second suspension point.

5. The system according to claim 4, wherein the support unit includes a second dimensionally stable support element which defines the distance between the first lower suspension point and the second lower suspension point at which the harness system is connected to the traction device and bridges the distance.

6. The system according to claim 1, wherein the support unit includes at least a first dimensionally stable support element which bridges the distance between the first suspension point and the second suspension point.

7. The system according to claim 6, wherein the support unit includes a second dimensionally stable support element which defines the distance between the first lower suspension point and the second lower suspension point at which the harness system is connected to the traction device and bridges the distance.

8. The system according to claim 7, wherein a first traction element is assigned to the first dimensionally stable support element, which connects the first dimensionally stable support element to a first abutment, and a second traction element is assigned to the second dimensionally stable support element, which connects the second dimensionally stable support element to a second abutment.

9. The system according to claim 8, wherein the first abutment and/or the second abutment have a height-adjustable and/or laterally adjustable anchorage.

10. The system according to claim 8, wherein the first abutment and/or the second abutment have a height-adjustable and/or laterally adjustable winch.

11. The system according to claim 8, wherein the first abutment and/or the second abutment have a winch with a height-adjustable and/or laterally adjustable deflecting device.

12. The system according to claim 1, wherein the traction element connects the support unit to an abutment.

13. The system according to claim 1, wherein the operating chair has a height-adjustable column between the seat and the base frame, at an upper end of which the seat is arranged to be inclinable.

14. The system according to claim 13, wherein the operating chair has, at a lower end of the height-adjustable column, a joint device which forms a pivot axis about which the operating chair is designed to pivot laterally.

15. A system for supporting a surgeon, comprising:

an operating chair with a base frame which can be placed on a floor, with a seat for the surgeon supported on the base frame; and a restraining device for the surgeon, having a harness system which has at least a first and a second restraining belt which are connected to at least a first suspension point and a second suspension point of a traction device, the first suspension point being spaced-apart from the second suspension point, wherein the traction device is arranged to set a distance between the first suspension point and the second suspension point;

further comprising a height-adjustable and/or laterally adjustable winch operably connected to one or more of the first suspension point and the second suspension point:

wherein the laterally adjustable winch has at least one electric gear motor.

16. The system according to claim 15, wherein the at least one electric gear motor is designed to be self-locking.

17. A system for supporting a surgeon, comprising:

an operating chair with a base frame which can be placed on a floor, with a seat for the surgeon supported on the base frame; and a restraining device for the surgeon, having a harness system which has at least a first and a second restraining belt which are connected to at least a first suspension point and a second suspension point of a traction device, the first suspension point being spaced-apart from the second suspension point, wherein the traction device is arranged to set a distance between the first suspension point and the second suspension point;

wherein the harness system further comprises a first shoulder strap connected to a first upper suspension point and a first lower suspension point of the traction device at a distance from each other, and a second shoulder strap, which is connected to a second upper suspension point and a second lower suspension point of the traction device at a distance from one another;

wherein the traction device has at least a first dimensionally stable support element which bridges the distance between the first suspension point and the second suspension point;

wherein the traction device has a second dimensionally stable support element which defines the distance between the first lower suspension point and the second lower suspension point at which the harness system is connected to the traction device and bridges the distance;

wherein the first dimensionally stable support element and the second dimensionally stable support element form a support unit which defines and bridges a distance between the first upper suspension point and the first lower suspension point, and a distance between the second upper suspension point and the second lower suspension point;

wherein a traction element connects the support unit to an abutment;

wherein the support unit includes a connecting device configured to variably define a connection point at which the traction element is connected to the support unit.

* * * * *